United States Patent

Mauro et al.

[11] Patent Number: 5,616,795
[45] Date of Patent: Apr. 1, 1997

[54] PROCESS FOR THE PREPARATION OF A DICARBOXYLIC ACID DICHLORIDE

[75] Inventors: Marina Mauro; Carlo F. Viscardi; Massimo Gagna, all of Mozzo, Italy

[73] Assignee: Fructamine S.p.A., Mozzo, Italy

[21] Appl. No.: 650,094

[22] Filed: May 17, 1996

[30] Foreign Application Priority Data

May 23, 1995 [IT] Italy .................. MI95A1044
Aug. 4, 1995 [IT] Italy .................. RM95A0550

[51] Int. Cl.⁶ .................................................. C07C 63/00
[52] U.S. Cl. ............................................................ 562/855
[58] Field of Search ............................................ 562/855

[56] References Cited

U.S. PATENT DOCUMENTS

| 4,001,323 | 1/1977 | Felder et al. | 260/559 |
| 4,348,377 | 9/1982 | Felder et al. | 424/5 |
| 4,396,598 | 8/1983 | Lin | 424/5 |
| 5,191,120 | 3/1993 | Kneller | 564/153 |

OTHER PUBLICATIONS

Chem Abtracts; 55:5884i Mar. 8, 1962.
Chem Abstracts; 55:24683g Nov. 17, 1961.
Chem Abstracts; 57:3367d Aug. 9, 1962.

*Primary Examiner*—Samuel Barts
*Attorney, Agent, or Firm*—Bucknam and Archer

[57] ABSTRACT

The present invention refers to a process for the preparation of 5-amino-2,4,6-triiodo-1,3-benzenedicarboxylic acid dichloride, comprising the reaction in heterogeneous phase between 5-amino-2,4,6-triiodo-1,3-benzenedicarboxylic acid and thionyl chloride, in a solvent selected from the group consisting of: ($C_7$–$C_{16}$) linear or branched hydrocarbons, ($C_7$–$C_8$) aromatic hydrocarbons, 1,1,1-trichloroethane, n-butylacetate, diglyme (diethylenglycoledimethylether), and in the presence of a catalytic amount of a tertiary amine.

14 Claims, No Drawings

PROCESS FOR THE PREPARATION OF A DICARBOXYLIC ACID DICHLORIDE

This invention refers to a new process for the synthesis of 5-amino-2,4,6-triiodo-1,3-benzenedicarboxylic acid dichloride of formula (I)

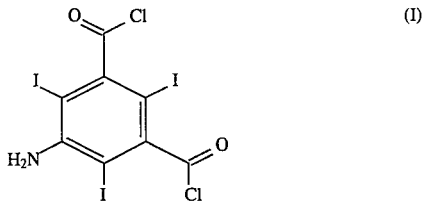

The compound of formula (I) is an useful intermediate for the preparation of iodinated X-ray contrast media.

The synthesis of said compound has been previously described, for instance in patents WO 9405337, WO 9109007, EP 118347, EP 83964, EP 23992, CH 616403, CH 608189, DE 2710730, DE 2547789.

In some references the reaction of 5-amino-2,4,6-triiodo-1,3-benzenedicarboxylic acid with thionyl chloride is described without addition of solvent (DE 2547789, DE 2710730, CH 608189, CH 616403, EP 23992), or with a small amount of dimethylformamide, as a catalyst (EP 118347): the resulting yields are satisfactory.

On the other hand the reaction carried out in thionyl chloride without solvent causes serious problems of industrial safety. If from one hand it is difficult to have a step-by-step loading of the starting product, which is a solid, in hot thionyl chloride, on the other hand the addition, the cold mixing of the two reagents and the successive heating can generate a fugitive reaction with unforeseeable effects.

In other references the reaction is carried out in ethyl acetate (WO 9405337, WO 9109007, EP 83964). In this case the declared yields drop sharply (50–60%).

From the industrial point of view it is very important to exploit a synthetic process which can be operated in safe operation conditions and leads to good yields of pure product without further purifications (crystallisation, and so on).

The process of this invention refers to the chlorination of 5-amino-2,4,6-triiodo-1,3-benzenedicarboxylic acid in heterogeneous phase in a solvent selected from the group consisting of: ($C_7$–$C_{16}$) linear or branched aliphatic hydrocarbons; ($C_7$–$C_8$) aromatic hydrocarbons, 1,1,1-trichloroethane, n-butylacetate, diglyme (diethylenglycoldimethylether), with catalytic amounts of tertiary amine.

Particularly preferred are the following conditions of chlorination, relative to the process of this invention:

the hydrocarbon is selected from the group of ($C_8C_{14}$) linear or branched hydrocarbons, said hydrocarbons are preferably n-octane, n-decane, n-dodecane, ligroin, kerosene;

the aromatic hydrocarbon is selected from the group of benzene substituted by methyl groups, preferably said aromatic hydrocarbons are toluene or xylene.

tertiary amine is selected from N-methyl-morpholine, triethylamine, quinoline, 2-, 3- or 4-dimethylamino pyridine, 2-ethyl-5-methylpyridine.

When the reaction of chlorination is carried out in ($C_7$–$C_{16}$) linear or branched aliphatic hydrocarbons the intermediate of formula (II), 5-sulphinylamino-2,4, 6-triiodo-1,3-benzenedicarboxylic acid dichloride can be isolated.

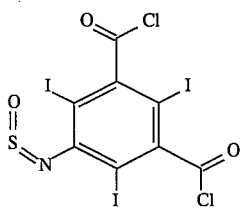

The process can be carried out either with or without isolation of said intermediate (II), obtaining in both cases analogous yields and purity in the final product.

This invention is also aimed to achieve an isolated product in high yield and with a high purity of the final product, through the addition to the reaction mixture, after completion of the chlorination reaction of 5-amino-2,4,6-triiodo-1, 3-benzenedicarboxylic acid, or to the isolated intermediate (II), of an amount of diglyme, so that the final mixture contains not less than 0.5 kg of diglyme/kg of the starting product and through the subsequent addition of water.

The following examples aim at describing the experimental conditions in order to perform the process of this invention.

EXAMPLE 1

5-amino-2,4,6-triiodo-1,3-benzenedicarboxylic acid dichloride

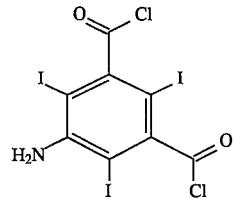

A) 5-amino-1,3-benzenedicarboxylic acid 325 g 5-nitro-1,3-benzenedicarboxylic acid (product available on the market) are loaded into a reactor with 2.8 l of water. It is heated to 60°–70° C. and the starting product dissolved by addition of 410 g of 30% NaOH. Then 10 g of charcoal are added; the slurry is filtered and the filter is washed with 200 ml of water.

8 g of Pd/C 5% (product available on the market) are then loaded and conditioned with aprox. 0.01 $m^3$ nitrogen. 0.1 $m^3$ hydrogen are added under a pressure of 30 kPa. The temperature spontaneously reaches 50° C. and is kept by cooling. When the hydrogen consumption stops, the solution is kept under pressure for 1 h and then the residual hydrogen is removed by washing with 0.02 $m^3$ of nitrogen. The suspension is filtered and the filter washed with 100 ml of water giving aprox. 3.85 kg of solution containing 5-amino-1,3-benzenedicarboxylic acid sodium salt.

B) 5-amino-2,4,6-triiodo-1,3-benzenedicarboxylic acid

In a reactor loaded with 2.75 l of water, are added in sequence 0.08 kg of HCl (34% w/w), 3.85 kg of solution of 5-amino-1,3-benzenedicarboxylic acid sodium salt coming from the previous reaction and 375 g of $H_2SO_4$ (1:1 aqueous solution). The content is heated to 70° C., and during 3 hours 1.35 kg of a solution of ICl in HCl (44.5% iodine, molar ratio ICl:HCl=1:1) (product available on the market) is added. When the addition is complete the solution is heated to 90° C. and the temperature kept for 6 h. Then the content is cooled to 60° C. and transferred to another reactor, where it is cooled to 30° C. The slurry is decolourised by adding 45 g of sodium bisulfite under stirring, then centrifuged and the product washed with 0.3 kg of water thus giving 935 g of the desired wet product. After drying, 830 g of the desired product are obtained.

Total yield of the two steps (on the anhydrous product): 95.0%

Water content: 2%

Potentiometric assay: 99.3%

$^1$H-NMR, $^{13}$C-NMR, IR and MS spectra are consistent with the structure.

C) 5-amino-2,4,6-triiodo-1,3-benzenedicarboxylic acid dichloride

A mixture of 1.2 kg of compound B) and 6 g of quinoline and 970 g of meta-xylene are heated at 65°–70° C., under stirring in a nitrogen atmosphere. Thereafter 500÷600 g of a SOCl$_2$/meta-xylene mixture containing 10% of this last one are added during 2 h, and then 1 kg of SOCl$_2$ is added in 4÷6 h, by keeping the temperature between 65° and 70° C. When the addition terminates the mixture is heated at 80°÷85° C. in 2 h and this temperature is kept for 6 h, in order to complete the reaction. Then the mixture is cooled at 40°÷50° C., the pressure is reduced to 100 mbar and a SOCl$_2$ meta-xylene mixture containing 10% of this last one is distilled off.

The pressure is then raised to 1 atm with nitrogen and always under nitrogen atmosphere and under stirring, 1.1 kg of diglyme is added while the temperature is kept between 40°÷50° C.

Thereafter the pH is kept to 2.5÷3 by adding 280÷240 g of NaOH (13÷15% aqueous solution). Then 300 g of water are added and the pH is kept to 6 by adding 690÷590 g of NaOH (13÷15% aqueous solution); the slurry is then diluted with 150÷180 g of water, at a temperature of 30° C.

The suspension is filtered under nitrogen atmosphere and the wet product is washed until the washing waters reach pH 7.

The product is dried at a temperature of 50°÷65° C., giving 1.180 kg of the desired product.

Yield calculated on anhydrous product: 92%

H$_2$O content: 1%

HPLC: 98.5%

Stationary phase: column E. Merck Lichrosphere$^R$ RP-18 5 μm 4 mm×12.5 cm

Mobile phase: gradient elution

| A = water | B = CH$_3$CN |
|---|---|
| min | % B |
| 0 | 60 |
| 3 | 60 |
| 12 | 80 |
| 19 | 80 |
| 20 | 60 |

Flow: 1.2 ml min$^{-1}$

Temperature: 30° C.,

UV detection: 240 nm $^1$H-NMR, $^{13}$C-NMR, IR and MS are consistent with the structure.

EXAMPLE 2

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using diglyme instead of meta-xylene, with quinoline. The desired product is isolated without any other addition of diglyme with a resulting yield of 82%.

The chemical-physical characteristics are accordance with those previously described.

EXAMPLE 3

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using diglyme instead of meta-xylene, with N-methyl-morpholine instead of quinoline. The desired product is isolated without further addition of diglyme to give a yield of 85.2%.

The chemical-physical characteristics are in accordance with those previously described.

EXAMPLE 4

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using diglyme instead of meta-xylene, with triethylamine instead of quinoline. The desired product is isolated without further addition of diglyme with a resulting yield of 89%.

The chemical-physical characteristics are accordance with those previously described.

EXAMPLE 5

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using diglyme instead of meta-xylene, with 2-ethyl-5methylpyridine instead of quinoline. The desired product is isolated without any further addition of diglyme with a resulting yield of 87.7%.

The chemical-physical characteristics are accordance with those previously described.

EXAMPLE 6

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using 2.2 kg of 1,1,1-trichloroethane instead of meta-xylene, with N-methyl-morpholine instead of quinoline. The mixture is treated with 5 kg of water. The precipitated solid is filtered, dissolved in diglyme and reprecipitated under the above mentioned conditions, giving a yield of 94.1%.

The chemical-physical characteristics are accordance with those previously described.

EXAMPLE 7

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using 2.2 kg of 1,1,1-trichloroethane instead of meta-xylene, with pyridine instead of quinoline. The mixture is filtered in 5 kg of water. The precipitated solid is filtered, dissolved in diglyme and reprecipitated under the above mentioned conditions, giving a yield of 93.4%.

The chemical-physical characteristics accordance with those previously described.

EXAMPLE 8

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using 2.2 kg of 1,1,1-trichloroethane instead of meta-xylene, with quinoline. The mixture is filtered in 5 kg of water. The precipitated solid is filtered and dissolved in diglyme and reprecipitated under the above mentioned conditions, giving a yield of 86.3%.

The chemical-physical characteristics are accordance with those previously described.

EXAMPLE 9

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using n-butylacetate instead of meta-xylene, and N-methyl-morpholine instead of quinoline. When the reaction is completed 300 g of thionyl/n-butylacetate chloride mixture are distilled, 1 kg of n-butylacetate is added, the mixture is cooled at 50° C. and 5 kg of water and 0.5 kg of $Na_2CO_3$ are added. The solid is filtered giving a yield of 91.7%.

The chemical-physical characteristics are accordance with those previously described.

EXAMPLE 10

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using kerosene instead of meta-xylene, with N-methyl-morpholine instead of quinoline, giving a yield of 95.2%.

The chemical-physical characteristics are accordance with those previously described.

EXAMPLE 11

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using ligroin instead of meta-xylene, with N-methyl-morpholine instead of quinoline, giving a yield of 89.4%.
The chemical-physical characteristics are in accordance with those previously described.

EXAMPLE 12

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using n-octane instead of meta-xylene, with N-methyl-morpholine instead of quinoline, giving a yield of 80.1%.

The chemical-physical characteristics are in accordance with those previously described.

EXAMPLE 13

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using n-decane instead of meta-xylene, with N-methyl-morpholine instead of quinoline, giving a yield of 94.8%.

The chemical-physical characteristics are in accordance with those previously described.

EXAMPLE 14

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using n-dodecane instead of meta-xylene, with N-methyl-morpholine instead of quinoline, giving a yield of 89.7%.

The chemical-physical characteristics are in accordance with those previously described.

EXAMPLE 15

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using n-dodecane instead of meta-xylene, with quinoline, giving a yield of 95.6%.

The chemical-physical characteristics are in accordance with those previously described.

EXAMPLE 16

Alternative preparation of 5-amino-2,4,6-triiodo-1,3-benzenedicarboxylic acid dichloride using linear or branched hydrocarbons($C_8$–$C_{14}$) with the isolation of the compound of formula (II)

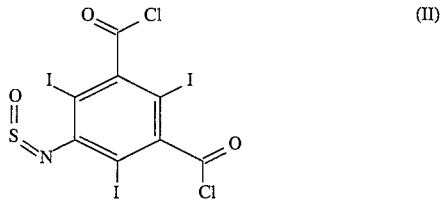

A) 5-Sulphinylamino-2,4,6-triiodo-1,3-benzenedicarboxylic acid dichloride

The preparation is carried out according to EXAMPLE 13 up to the distillation of $SOCl_2$/aliphatic hydrocarbon mixture which contains 10% of this last one. Now the solid can be filtered under nitrogen atmosphere, washed with hydrocarbon solvent, and dried under reduced pressure at 100 Pa and 55° C., thus giving 1.23 kg of 5-sulphinylamino-2,4,6-triiodo-1,3-benzenedicarboxylic acid dichloride.

Yield: 92%

HPLC: 95%

Iodometric values (solution of $I_{2, 0.1}N$, item 9910 Merck): 94%

| Elemental analysis | C | N | S | Cl | I |
|---|---|---|---|---|---|
| % calculated: | 14.97 | 2.18 | 5.00 | 11.05 | 59.32 |
| % found: | 15.10 | 2.16 | 4.96 | 11.00 | 58.95 |

$^1$H-NMR, $^{13}$C-NMR, IR and MS are consistent with the structure.

B) 5-Amino-2,4,6-triiodo-1,3-benzenedicarboxylic acid dichloride 1.23 kg of the compound A) are dissolved in 1.1 kg of diglyme at 40° C. The solution is then processed according to the procedure described in EXAMPLE 1C. 1.17 kg of the desired compound are obtained.

Yield: 91%

The chemical-physical characteristics are in accordance with those previously described.

EXAMPLE 17

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using toluene instead of meta-xylene, with N-methyl-morpholine instead of quinoline, giving a yield of 90.1%.

The chemical-physical characteristics are in accordance with those previously described.

EXAMPLE 18

5-amino-2,4,6-triiodo-1,3-benzenedicarboxylic acid dichloride.

According to the procedure described in Example 1, the reaction is carried out with the same amounts of 5-amino-2,4,6-triiodo-1,3-benzenedicarboxylic acid using toluene instead of meta-xylene, with quinoline, giving a yield of 92.3%.

The chemical-physical characteristics are in accordance with those previously described.

We claim:

1. A process for the preparation of 5-amino-2,4, 6-triiodo-1,3-benzenedicarboxylic acid dichloride, comprising the reaction in heterogeneous phase between 5-amino-2,4,6-triiodo-1,3-benzenedicarboxylic acid and thionyl chloride, in a solvent selected from the group consisting of: ($C_7$–$C_{16}$) linear or branched hydrocarbons, ($C_7$–$C_8$) aromatic hydrocarbons, 1,1,1-trichloroethane, n-butylacetate, diglyme (diethylenglycoledimethylether), and in the presence of a catalytic amount of a tertiary amine.

2. The process according to claim 1, in which said aromatic hydrocarbon is toluene.

3. The process according to claim 1, in which said aromatic hydrocarbon is meta-xylene.

4. The process according to claim 1, in which said linear or branched hydrocarbon is selected from ($C_8$–$C_{14}$) linear or branched hydrocarbons.

5. The process according to claim 4, in which said hydrocarbon is n-octane.

6. The process according to claim 4, in which said hydrocarbon is n-decane.

7. The process according to claim 4, in which said hydrocarbon is n-dodecane.

8. The process according to claim 4, in which said hydrocarbon is kerosene.

9. The process according to claim 4, in which said hydrocarbon is ligroin.

10. The process according to claim 1, in which the tertiary amine is selected from the group consisting of N-methylmorpholine, triethylamine, quinoline, dimethylaminopyridine, 2-ethyl-5-methylpyridine.

11. The process according to claim 4, in which the intermediate of the chlorination reaction, that's to say 5-sulphinylamino-2,4,6-triiodo-1,3-benzenedicarboxylic acid dichloride is isolated through filtration from the reaction mixture and is successively transformed into 5-amino-2,4,6-triiodo-1,3-benzenedicarboxylic acid dichloride through water treatment.

12. 5-sulphinylamino-2,4,6-triiodo-1,3-benzenedicarboxylic acid dichloride of formula (II),

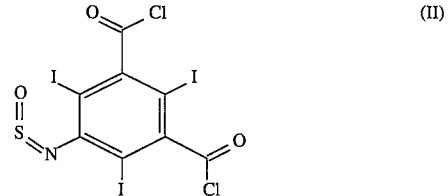

as intermediate for the process according to claim 1.

13. The process according to claim 1, in which an amount of diglyme greater than 0.5 kg of diglyme/kg of starting product is added to the reaction mixture, after completion of the chlorination reaction of 5-amino-2,4,6-triiodo-1,3-benzenedicarboxylic acid and successively treated with water to give 5-amino-2,4,6-triiodo-1, 3-benzenedicarboxylic acid dichloride.

14. Process for the preparation of 5-amino-2,4, 6-triiodo-1,3-benzenedicarboxylic acid dichloride, comprising the following steps:

a) catalytic hydrogenation of 5-nitro-1,3-benzenedicarboxylic acid in neutral or basic environment, which gives an aqueous solution of 5-amino-1,3-benzenedicarboxylic acid sodium salt;

b) direct iodination of the 5-amino-1,3benzenedicarboxylic acid sodium salt solution deriving from step a), without further purification, with a solution of ICl in HCl, being the 5-amino-1,3-benzenedicarboxylic acid sodium salt solution previously added with HCl and $H_2SO_4$ to give 5-amino-2,4,6-triiodo-1,3-benzenedicarboxylic acid;

c) reaction in heterogeneous phase between 5-amino-2,4,6-triiodo-1,3-benzenedicarboxylic acid and thionyl chloride, in a solvent selected from the group consisting of: ($C_7$–$C_{16}$) linear or branched hydrocarbons, (C7–$C_8$) aromatic hydrocarbons, 1,1,1trichloroethane, n-butylacetate, diglyme (diethylenglycoledimethylether), and in the presence of a catalytic amount of a tertiary amine.

* * * * *